(12) United States Patent
Deshpande et al.

(10) Patent No.: US 9,259,401 B2
(45) Date of Patent: Feb. 16, 2016

(54) WATER SOLUBLE COMPOSITION COMPRISING CURCUMIN HAVING ENHANCED BIOAVAILABILITY AND PROCESS THEREOF

(75) Inventors: Jayant Venkatesh Deshpande, Navi Mumbai (IN); Shrinivas Krishnarao Kulkarni, Santacruz (IN)

(73) Assignee: OMNIACTIVE HEALTH TECHNOLOGIES LTD., Prabhadevi (IN)

( * ) Notice: Subject to any disclaimer, the term of this patent is extended or adjusted under 35 U.S.C. 154(b) by 0 days.

(21) Appl. No.: 13/995,743

(22) PCT Filed: Jul. 22, 2011

(86) PCT No.: PCT/IN2011/000486
§ 371 (c)(1),
(2), (4) Date: Jun. 19, 2013

(87) PCT Pub. No.: WO2012/156979
PCT Pub. Date: Nov. 22, 2012

(65) Prior Publication Data
US 2013/0274343 A1    Oct. 17, 2013

(30) Foreign Application Priority Data
May 16, 2011   (IN) .................. 1487/MUM/2011

(51) Int. Cl.
*A61K 47/44* (2006.01)
*A61K 9/16* (2006.01)
*A61K 31/12* (2006.01)
*A61K 47/22* (2006.01)

(52) U.S. Cl.
CPC .............. *A61K 31/12* (2013.01); *A61K 9/1635* (2013.01); *A61K 9/1694* (2013.01); *A61K 47/22* (2013.01); *A61K 47/44* (2013.01)

(58) Field of Classification Search
None
See application file for complete search history.

(56) References Cited

U.S. PATENT DOCUMENTS

| | | | |
|---|---|---|---|
| 5,861,415 A | 1/1999 | Majeed et al. | |
| 7,879,373 B2 | 2/2011 | Antony | |
| 8,198,324 B2 | 6/2012 | Fortin | |
| 8,222,295 B2 | 7/2012 | Fortin | |
| 2003/0113388 A1* | 6/2003 | Phan ............................ | 424/756 |
| 2004/0146551 A1 | 7/2004 | Mannino et al. | |
| 2005/0058733 A1 | 3/2005 | Ochiai et al. | |
| 2005/0153976 A1* | 7/2005 | Fang et al. ................ | 514/253.11 |
| 2008/0138417 A1* | 6/2008 | Grigsby ..................... | 424/489 |
| 2009/0004334 A1* | 1/2009 | Nair .............................. | 426/74 |
| 2009/0131373 A1 | 5/2009 | Giori et al. | |
| 2009/0291102 A1 | 11/2009 | Fortin | |
| 2009/0324703 A1 | 12/2009 | Frautschy et al. | |
| 2010/0179103 A1 | 7/2010 | Desai | |
| 2010/0196496 A1 | 8/2010 | Fortin | |
| 2012/0195932 A1 | 8/2012 | Mannino et al. | |
| 2012/0208884 A1 | 8/2012 | Fortin | |
| 2012/0213823 A1 | 8/2012 | Fortin | |
| 2012/0213872 A1 | 8/2012 | Fortin | |
| 2012/0251582 A1 | 10/2012 | Fortin | |

FOREIGN PATENT DOCUMENTS

| | | |
|---|---|---|
| CN | 1568944 | 1/2005 |
| CN | 101671244 A * | 3/2010 |
| IN | 1827/DEL/2008 | 3/2010 |
| IN | 1776/DEL/2008 | 4/2010 |
| JP | 2003-113117 A | 4/2003 |
| JP | 2003-245054 A | 9/2003 |
| JP | 2005-281278 A | 10/2005 |
| JP | 2006-514103 A | 4/2006 |
| JP | 2006-327970 A | 12/2006 |
| JP | 2008-247809 | 10/2008 |
| KR | 10-2009-0083149 A | 8/2009 |
| WO | WO 2004/041247 A2 | 5/2004 |
| WO | WO 2007/103435 A2 | 9/2007 |
| WO | WO 2008/113177 A1 | 9/2008 |
| WO | WO 2009/101263 A2 | 8/2009 |
| WO | WO 2009/144220 A1 | 12/2009 |

OTHER PUBLICATIONS

Google translation of CN101671244A which was published in 2010.*
Sibel Roller et al, "Handbook of Fat Replacers", p. 135 (1996): [retrieved by on-line on Aug. 20, 2014 from website: http://books.google.com/books?id=wP8l58oKtisC&pg=PA135&lpg=PA135&dq=microcrystalline+cellulose+is+a+purified,+naturally+occurring&source=bl&ots=cYMWJp1COJ&sig=tNHXGxDJo1lbl0e74L2LvUrgkyU&hl=en&sa=X&ei=0af0U9XIOPXKsQSj_IA4&ved=. . . .*
Written Opinion for International Application No. PCT/IN2011/000486, European Patent Offiec, Netherlands, mailed Jan. 24, 2012.
International Search Report for International Application No. PCT/IN2011/000486, European Patent Office, Netherlands, mailed Jan. 24, 2012.

(Continued)

Primary Examiner — Ernst V Arnold
Assistant Examiner — Kyung Sook Chang
(74) Attorney, Agent, or Firm — Sterne, Kessler, Goldstein & Fox P.L.L.C.

(57) ABSTRACT

The invention disclosed relates to a water-soluble composition having enhanced bioavailability useful for the treatment of depression which comprises a synergistic combination of curcumin, at least an antioxidant, a hydrophilic carrier and a fat. The invention also discloses a process for the preparation of the curcumin composition which comprises the steps of dissolving curcumin, at least one antioxidant, a hydrophilic carrier and a fat in a solvent to form a homogenous mass; warming the resultant mass at a temperature ranging from 25° C. to 60° C. for a period of 4 to 8 hours to obtain a dry wet mass; removing the solvent by evaporation to form dry mass and pulverizing the dry mass to form a fine powder.

19 Claims, 8 Drawing Sheets

(56) References Cited

OTHER PUBLICATIONS

Kulkarni, S.K., et al., "Antidepressant activity of curcumin: involvement of serotonin and dopamine system," *Psychopharmacology* 201:435-442, Springer-Verlag, Germany (2008).

Kulkarni, S.K., et al., "Potentials of Curcumin as an Antidepressant," *The Scientific World Journal* 9:1233-1241, Scientific World, Inc., England (2009).

Li, Y-C., et al., "Antidepressant-like effects of curcumin on serotonergic receptor-coupled AC-cAMP pathway in chronic unpredictable mild stress of rats," *Progress in Neuro-Psychopharmacology & Biological Psychiatry* 33:435-449, Elsevier Inc., United States (2009).

Xu, Y., et al., "Antidepressant effects of curcumin in the forced swim test and olfactory bulbectomy models of depression in rats," *Pharmacology, Biochemistry and Behavior* 82:200-206, Elsevier Inc., United States (2005).

Xu, Y., et al., "Curcumin reverses impaired hippocampal neurogenesis and increases serotonin receptor 1A mRNA and brain-derived neurotrophic factor expression in chronically stressed rats," *Brain Research* 1162:9-18, Elsevier B.V., Netherlands (2007).

Yu, Z.F., et al., "Antidepressant activity of aqueous extracts of *Curcuma longa* in mice," *Journal of Ethnopharmacology* 83:161-165, Elsevier Science Ireland Ltd., Ireland (2002).

Ørgaard, A. and Jensen, L., "The effects of soy isoflavones on obesity," *Experimental Biology and Medicine* 233(9): 1066-1068, Society for Experimental Biology and Medicine, United States (2008).

Handbook of Pharmaceutical Excipients, $6^{th}$ ., Raymond C. Rowe et al., eds., pp. 685-691, Pharmaceutical Press, United States (2009).

English language Translation of Japanese Patent Publication No. JP 2005-281278A (listed as document FP8 on accompanying form PTO/SB/08A).

English language Translation of Japanese Patent Publication No. JP 2006-327970A (listed as document FP9 on accompanying form PTO/SB/08A).

English language Translation of Japanese Patent Publication No. JP 2003-113117A (listed as document FP10 on accompanying form PTO/SB/08A).

English language Translation of Japanese Patent Publication No. JP 2006-514103A (listed as document FP11 on accompanying form PTO/SB/08A).

* cited by examiner

FIG. 8 - Mean AUC Graph Comparison
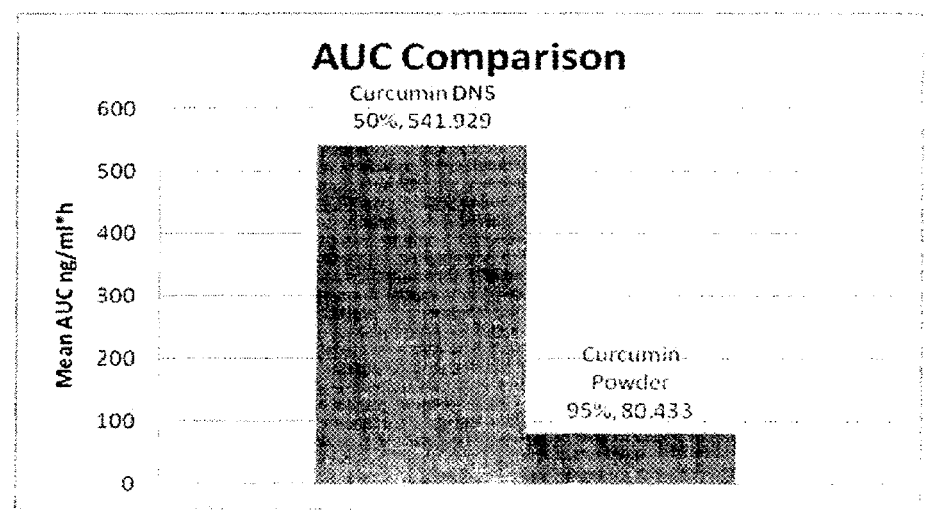

WATER SOLUBLE COMPOSITION COMPRISING CURCUMIN HAVING ENHANCED BIOAVAILABILITY AND PROCESS THEREOF

CROSS-REFERENCE TO RELATED APPLICATIONS

This application is the National Stage of International Application Number PCT/IN2011/000486, filed Jul. 22, 2011, which claims the benefit of Indian Application No. 1487/MUM/2011, which is incorporated by reference herein.

FIELD OF THE INVENTION

The present invention relates to a water soluble composition having enhanced bioavailability and a process for its preparation. More particularly, the invention relates to a novel water soluble composition containing curcumin along with at least one antioxidant, a hydrophilic carrier and a fat, having enhanced bioavailability.

The composition of the present invention is useful for the treatment of depression by alleviating symptoms of depression in humans. The novel water soluble composition of curcumin of the present invention having enhanced bioavailability is particularly useful for formulating into oral delivery forms such as dry mixes, tablets, capsules etc.

BACKGROUND OF THE INVENTION

Curcumin [1,7-bis(4-hydroxy-3-methoxyphenyl)-1,6-heptadien-3,5-dione] is a hydrophobic polyphenol derivative which is a potent antioxidant derived from the spice turmeric. Commercial curcumin contains approximately, 77% diferuloylmethane, 17% demethoxycurcumin, and 6% bis-demethoxycurcumin. Curcumin is a major active ingredient of *Curcuma Longa* which has been used since time immemorial. *Curcuma longa* (turmeric) is a well known indigenous herbal medicine. It is known for its diverse biological actions and pharmacological activities including anti-inflammatory, antioxidant, antiproliferative, antimicrobial, anticarcinogenic and antiangiogenic properties.

Major depression, a debilitating psychiatric disorder, today is considered as one of the most prevalent human illness. It may be caused by numerous reasons which include persistence of social, occupational, financial and interpersonal difficulties. A person with depression usually exhibits a state of sadness of mood and aversion to usual activities which generally affect a person's thoughts, behaviour, feeling and physical well being.

Various antidepressants have been prescribed for alleviating the symptoms of depression. Currently used drugs mainly include monoamine oxidase inhibitors (MAOIs), tricyclic antidepressants (TCAs), tetracyclic antidepressants (TeCAs), selective serotonin reuptake inhibitors (SSRIs), and Norepineprine dopamine reuptake inhibitors (NDRIs). Some of the blockbuster drugs indicated for treatment of depression which are available in the market are sold under the brands Prozac, Norpramin, Effexor, Serzone, Remeron, Desyrel, Zolsoft, paxil, Pamelor, Aventyl, Surmontil etc. Nuetraceutical products such as St Johns Wort have also been widely used for depression.

However, the therapeutic benefits of the aforementioned drugs are often accompanied by unwanted side effects and the precise mechanisms of action are not well understood. The plethora of associated side effects include nausea, insomnia, anxiety, restlessness, decreased sex drive, dizziness, weight gain or loss, tremors, sweating, sleepiness, fatigue, dry mouth, diarrhoea, constipation, headaches etc. Owing to these side effects and failure of some patients to respond to the already existing drugs, emphasizes the need for safer and efficacious drugs for treatment of major depression.

Therefore, it would be useful to identify a composition from traditional herbs or of herbal origin that would specifically address issues of safety and efficacy, thereby alleviating depressive symptoms. Curcumin is one such molecule that has shown promising efficacy in various animal models of major depression. Although the mechanism of the antidepressant effect of curcumin is not fully understood, it is hypothesized to act through inhibiting the monoamine oxidase enzyme and modulating the release of serotonin and dopamine. Moreover, evidences have shown that curcumin enhances neurogenesis, notably in the frontal cortex and hippocampal regions of the brain. (S K Kulkarni et al. Potentials of Curcumin as an Antidepressant; Scientific World Journal 2009 Nov. 1; 9:1233-41).

Another study confirmed the antidepressant effects of curcumin in the forced swim test which suggested that the antidepressant effects may be mediated by actions in the central monoaminergic neurotransmitter systems. Curcumin doses of 1.25, 2.5, 5 and 10 mg/kg P.O. were used in the forced swim test on rats and chronic treatment with curcumin for 14 days showed to have reduced the immobility time in the forced swim test (Ying Xu et al. Antidepressant effects of curcumin in the forced swim test and olfactory bulbectomy models of depression in rats. Pharmacology Biochemistry and behaviour. 82 (1) 2005. pp. 200-206).

Oral administration of aqueous turmeric extracts (140 to 560 mg/kg P.O.) for 14 days has shown reduction in immobility in tail suspension and forced swim tests. Results suggest that turmeric extract had specific antidepressant effects in vivo (Z F Yu, L D Kong and Y Chen. Antidepressant activity of aqueous extracts of *Curcuma longa* in mice. Journal of ethnopharmacology. 83 (1-2) 2002. pp. 161-165).

Studies show that stress induced damage to hippocampal neurons may contribute to the pathophysiology of depression. Curcumin administration (10 and 20 mg/kg, P.O.) increased hippocampal neurogenesis in chronically stressed rats, it shows similar activity of classic antidepressant imipramine treatment (Ying Xu et al. Curcumin reverses impaired hippocampal neurogenesis and increases serotonin receptor 1A mRNA and brain-derived neurotrophic factor expression in chronically stressed rats. Brainsearch. 1162 (2007) 9-18).

Another study investigates the involvement of monoaminergic systems in the antidepressant activity of curcumin and the effect of piperine, a bioavailability enhancer, on the bioavailability and the biological effects of curcumin. The study indicates that curcumin dose inhibited the immobility period, increases serotonin (5-HT) as well as dopamine levels and inhibited the monoamine oxidase enzymes in mice. The coadministration of piperine with curcumin resulted in the potentiation of pharmacological, biochemical and neurochemical activities (S K Kulkarni et al. Antidepressant activity of curcumin: involvement of serotonin and dopamine system. Psychopharmacology (2008) 201: 435-442).

AC-cAMP second messenger pathway has recently been suggested to play an important role in depression. Therefore, a compound that regulates the signal pathway may have potential as an antidepressant. Effects of chronic unpredictable mild stress (CUMS) and curcumin on behaviours/serotonergic receptor-coupled AC-cAMP signal pathway have been studied in rats. Curcumin enhanced AC activity and c-AMP levels in platelet and various brain regions, and up-regulated mRNA expressions of AC subtypes AC 2, AC 8 and cAMP response element binding protein (CREB) in the hippocampus, cortex and hypothalamus of the CUMS rats. The potent antidepressant property of curcumin might be attributed to its improvement of AC-cAMP pathway as well as CREB via suppressing central 5-HT (1A/1B/7) receptors in the CUMS rats (Y C Li et al. Antidepressant-like effects of curcumin on serotonergic receptor-coupled AC-cAMP pathway in chronic unpredictable mild stress of rats. Prog Neuropsychopharmacol Biol Psychiatry. 2009 Apr. 30; 33(3): 435-49).

In addition to the above, there are a number of clinical studies dealing with the efficacy of curcumin in humans. Despite the clinical data showing a strong intrinsic activity suggesting the potential of curcumin being used as a therapeutic agent, the use of curcumin in clinics for the treatment for a number of ailments including major depression is limited due to its poor gastrointestinal absorption.

The reasons for reduced bioavailability of any agent within the body may be attributed to low intrinsic activity, poor absorption, high rate of metabolism, inactivity of metabolic products and/or rapid elimination and clearance from the body. Studies on curcumin relating to absorption, distribution, metabolism and excretion of curcumin have revealed poor absorption and rapid metabolism of curcumin severely curtails its bioavailability.

WO2007/103435 discloses curcuminoid formulations having enhanced bioavailability comprising of a curcuminoid, antioxidant, glucuronidation inhibitor, and water-soluble, pharmaceutically acceptable inhibitor which are useful for treating Alzheimer's disease and other age-related disorders.

WO2008/113177 discloses various compounds and compositions comprising polyunsaturated fatty acid monoglycerides and derivatives thereof. These compounds have been indicated as useful for enhancing solubility of various active agents and enhancing their bioavailability.

Indian application no. 1776/DEL/2008 discloses a pharmaceutical composition of curcuminiods with higher drug loading ability, improved bioavailability having adequate physical and chemical stability as a self nanoemulsifying composition.

Yet another Indian patent application no. 1827/DEL/2008 provides for curcumin nanoparticles and curcumin bound to chitosan nanoparticles and methods of producing the same. The bioavailability of curcumin in these formulations was shown to improve by more than 10 fold.

There are several limitations of these compositions such as excessive damage to curcumin in the intestine through cytochromes, reduction of curcumin level in serum due to continuous metabolism in liver resulting in the formation of less potent curcumin glucuronide and sulphates, and difficulty in crossing the blood brain barrier. For these reasons, none of the current technologies have been successful commercially as a remedy for mental depression or as a mood elevator.

Currently used antidepressant drugs have many limitations. Apart from being prescription drugs, requiring a continuous medical supervision during treatment, they have serious side effects. Selective serotonin reuptake inhibitors have side effects such as nausea, diarrhea, agitation, loss of sexual drive, etc. Tricyclic inhibitors have side effects such as dry mouth, blurred vision, dizziness, tremors, etc., Monoamino oxidase inhibitors have side effects such as hepatitis, heart attack, stroke, seizures, etc. Curcumin being from dietary source is free from such serious side effects.

OBJECTIVES OF THE INVENTION

Therefore, the main objective of the present invention is to provide a novel water-soluble composition having enhanced bioavailability useful as an antidepressant in humans.

Another objective of the present invention is to provide a novel water-soluble composition having enhanced bioavailability containing curcumin which is available in an orally administrable form.

Yet another objective of the present invention is to provide a novel water-soluble composition having enhanced bioavailability containing curcumin, useful as an antidepressant in humans which is safer for human consumption without any side effects.

Still another objective of the present invention is to provide a novel water-soluble composition having enhanced bioavailability containing curcumin useful as an antidepressant in humans which has better efficacy than the conventional antidepressants.

Still another objective of the present invention is to provide a process for the preparation of a novel water-soluble composition containing curcumin having enhanced bioavailability useful as an antidepressant in humans.

The present invention has been developed based on our findings due to sustained R & D carried out by us due to the fact that when curcumin is combined with an antioxidant, a hydrophilic carrier and a fat, the bioavailability of curcumin is surprisingly enhanced. Such a combination resulting in enhanced bioavailability, useful for alleviating symptoms of depression is not hitherto known.

SUMMARY OF THE INVENTION

Accordingly, the present invention provides a novel water-soluble composition having enhanced bioavailability useful for the treatment of depression which comprises a synergistic combination of curcumin, at least an antioxidant, a hydrophilic carrier and a fat.

According to another aspect of the present invention there is provided a process for the preparation of a novel water-soluble composition having enhanced bioavailability useful for treating depression which comprises:

(i) dissolving curcumin, at least one antioxidant, a hydrophilic carrier and a fat in a solvent to form a homogenous mass;
(ii) warming the resultant mass at a temperature ranging from 25° C. to 60° C. for a period of 4 to 8 hours to obtain a dry wet mass;
(iii) removing the solvent by evaporation to form dry mass and
(iv) pulverizing the dry mass to form a fine powder.

BRIEF DESCRIPTION OF THE FIGURES

FIG. 8 shows data for the mean AUC for Curcumin Ultrasol Nutrient System 50% and Curcumin extract powder 95%.

DETAILED DESCRIPTION

Figure 1:
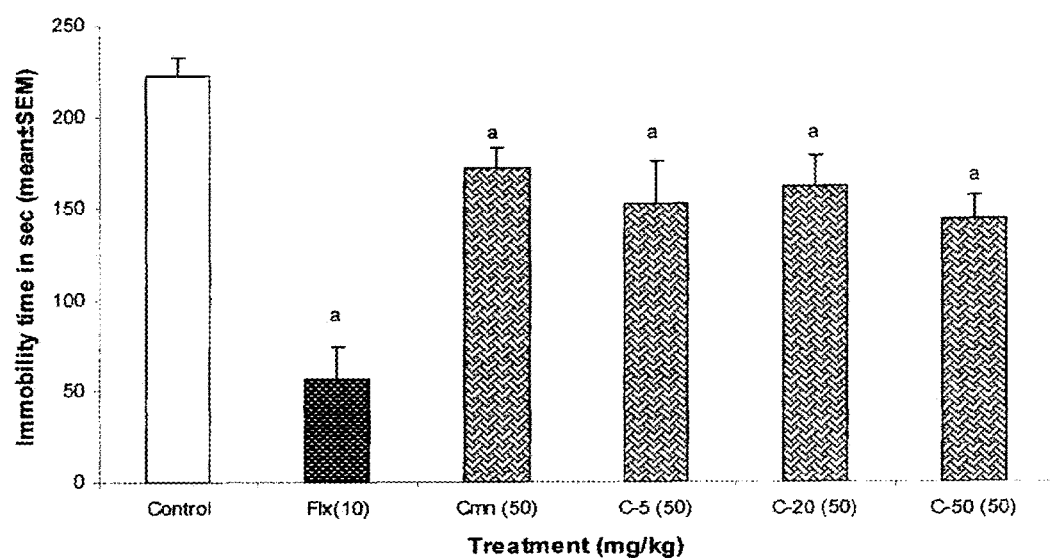
FIG. 1 shows data for immobility period and percentage decrease in the immobility of animals when administered with curcumin (conventional) and the compositions of the present invention, i.e., 2502-DNS-5B (C-5); 2502-DNS-20B (C-20) and 2502-DNS-50B (C-50), at a dose of 50 mg/kg.

Curcumin used in the step (i) can be commercially available one with an assay ranging between 85-96%. It can also be an extract of turmeric rich in curcumin. The amount of curcumin added may be sufficient to produce a water soluble curcumin with an assay of 1-55% curcumin.

The antioxidants used in step (i) can be selected from natural tocopherols, ascorbyl palmitate, rosemary extract, epigallocatechin gallate, catechins, ascorbic acid and mixture thereof. The amount of antioxidant used may range between 1-10%.

The hydrophilic carrier used in the step (i) can be selected from soluble starch, hydroxy propyl methyl cellulose, sodium carboxy methyl cellulose, polyvinyl pyrrolidone, polyethylene glycols 200-20000, glycerol, sorbitol, mannitol, glucose, sugar and mixture thereof. The quantity of hydrophilic carrier added may range between 10-90%.

The fat used in the step (i) may be selected from milk fat, medium chain triglycerides, long chain triglycerides, hydrogenated vegetable oils, and mixtures thereof. The quantity of fat used may range from 1-25%.

The solvent used for dissolving in the step (i) may be selected from isopropyl alcohol, acetone, methanol, alcohol, and mixtures thereof. The temperature maintained for obtaining an homogenous mass may range from ambient to 70 deg C.; preferably 25° C. to 60° C.

The removal of solvent in step (ii) can be performed in vacuum distillation or evaporation technique, or by spray drying technique. The resultant dry mass is pulverized by using mortar and pestle, mixer-grinder, multi-mill, ball mill, jet mill and the like.

The beneficial effects of curcumin have been well known. However, there are many problems associated with the bioavailability of curcumin when delivered in the oral form. Major portion of ingested curcumin is excreted through the feces unmetabolized and the small portion that gets absorbs is converted into other metabolites and excreted. Curcumin does not easily penetrate the gastrointestinal tract and is subject to liver and other intestinal enzymes. Owing to these enzymes, the curcumin within the body is rapidly metabolised thus reducing its bioavailability in the body. The small amount of curcumin that enters the bloodstream is rapidly metabolized by the liver and kidney. Therefore, although curcumin is highly lipophilic (and so easily crosses the blood brain barrier), only very small amounts of orally administered curcumin are registered in the serum and in the brain tissue.

Cytochrome P450 is a phase I metabolizing isoenzyme which is required for metabolizing toxic chemicals such as heterocyclic amines to induce DNA adduct formation leading to carcinogenesis. Curcumin when ingested in the body enters the gastrointestinal tract and is found to inhibit Cytochrome P450. As mentioned hereinabove, there have been studies carried out to increase the bioavailability of curcumin when used along with piperine. Piperine is a bioenhancer which inhibits Cytochrome P450 and thereby prevents metabolism of curcumin in the body. The composition of the present invention is seen to enhance the bioavailability without the presence of any additional bioenhancer.

The water soluble composition of curcumin of the present invention comprises of an antioxidant, a hydrophilic carrier and a fat. The antioxidant along with curcumin inhibits the Cytochrome P450. On the other hand, the presence of fat coating on the composition prevents the composition from attack by liver microsomal or other intestinal enzymes as these enzymes attack only aqueous compounds. Thus, the antioxidant and the fat play a vital role in enhancing the bioavailability of curcumin.

The details of the present invention are described in the Examples given below which are provided to illustrate the invention and therefore should not be construed to limit the scope of the present invention.

Example 1

18 g of curcumin (95%), 0.75 g of ascorbyl palmitate, 1.1 g of Green tea extract containing 0.55 g of EGCG, 0.8 G of natural tocopherol, 10 g of HPMC, 265 g of polyvinyl pyrrolidone (K 30) and 30 g of Medium Chain Triglyceride were suspended in 600 g of isopropyl alcohol to obtain a homogenous mass. The resultant homogenous mass was then heated to 70 deg C. to obtain a dry wet mass which was then subjected to distillation under the reduced pressure 600 mm Hg for removing isopropyl alcohol to obtain a dry mass. The dried mass was then pulverized in a mixer-grinder to form a fine yellow water-soluble powder containing 5.8% of curcumin.

Example 2

72 g of curcumin (95%), 8 g of natural tocopherol, 6 g of ascorbyl palmitate, 18 g of hydroxypropyl methyl cellulose, 15 g of hydrogenated soybean oil, and 200 g of mannitol were suspended in 500 g of ethyl alcohol to obtain a mixture. The mixture was then homogenized and heated at 60 deg C. to obtain a homogenized mass. This homogenized mass was subjected to evaporation under vacuum for removing ethyl alcohol to yield 317 g of dried mass. The resultant dry mass was then pulverized in a mortar with a pestle to yield a yellow powder with 20.1% curcumin.

Example 3

275 g of curcumin (95%), 5 g of Green tea Extract containing 50% EGCG, 10 g of ascorbyl palmitate, 30 g of Medium Chain Triglyceride, 20 g of hydrogenated soybean oil, and 175 g of Polyvinyl pyrrolidone were suspended in 500 g of ethyl alcohol. The mixture was homogenized and heated at 60 deg C. The resultant mixture is then subjected to evaporation under vacuum for removing ethyl alcohol to yield 520 g of dried mass. The resultant dried mass was then pulverized in a mortar with a pestle to yield a yellow powder with 51.3% curcumin.

Example 4

274 g of curcumin (95%), 5.1 g of Green tea Extract containing 50% EGCG, 10.6 g of ascorbyl palmitate, 31 g of Medium Chain Triglyceride, 20 g of hydrogenated soybean oil, and 175 g of Polyethylene Glycol 6000 were suspended in 500 g of acetone. The mixture was homogenized and heated at 55 deg C. to obtain a homogenized mass. The resultant mixture was subjected to evaporation of acetone under vacuum to yield 523 g of dried mass. The mass was then pulverized in a mortar with a pestle to yield a yellow powder with 50.6% curcumin.

Example 5

Antidepressant Activity of Curcumin

Test Procedures
Animals: Male Laca mice
Method: Porsolt Forced Swim test (also called behavioural despair test)

It is a test used to measure the effect of antidepressant drugs on the behaviour of laboratory animals, typically rats or mice. Animals are subjected to two trials during which they are force to swim in an acrylic glass cylinder filled with water and from which they cannot escape. The first trial lasts 15 minutes. Then, after 24-hours, a second trial is performed which lasts 5 minutes. The time that the animal spends without moving in the second trial is measured. This immobility time is decreased by antidepressants.

Male laca mice which have been housed under standard laboratory conditions with free access to feed and water are placed in a rectangular glass jar (25×12×25 cm3) containing 15 cm of water maintained at 24±1° C. After some time, the mice give up the attempt to escape from the water and subside into immobility. The duration of the immobility is measured. An animal was considered to be immobile whenever it remained floating passively in the water in a slightly hunched but upright position, its nose above the water surface. Many antidepressants have been shown to shorten the duration of the immobility when they are administered to the mouse. The total immobility period during the 6-min test was recorded with the help of stopwatch.

Test Substances: The following drugs were used:
1. Conventional Curcumin powder (C-C),
2. The compositions of the present invention are prepared by the process illustrated in Examples 1 to 4. The percentage of the curcumin dry nutrient system (hereinafter referred to as DNS) composition used in the given examples are 5%, 20%, and 50% and are denoted as follows in the example 5 to 6—DNS 5% as 2502-DNS-5B (C-5); DNS 20% as 2502-DNS-20B (C-20) and DNS 50% as 2502-DNS-50B (C-50) supplied by the applicant;
3. Other commercially available anti depression test drugs such as Flouxetine; Venlafaxine, Desipramine and Tranylcypromine.

A. Test for Antidepressant Activity of Curcumin

Figure 2:
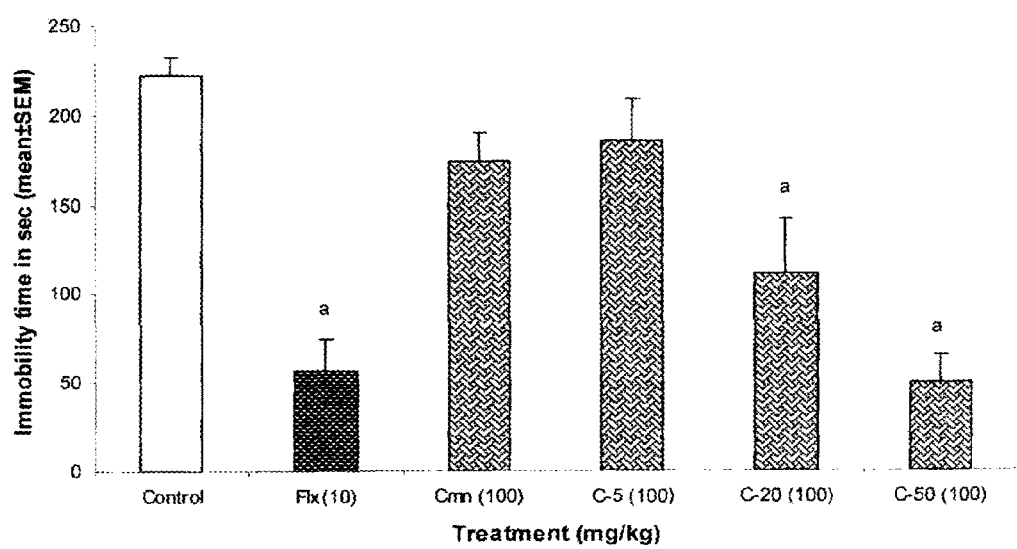
FIG. 2 shows data for immobility period and percentage decrease in the immobility of animals when administered with curcumin (conventional) and the compositions of the present invention, i.e., 2502-DNS-5B (C-5); 2502-DNS-20B (C-20) and 2502-DNS-50B (C-50), at a dose of 100 mg/kg.
Figure 3:
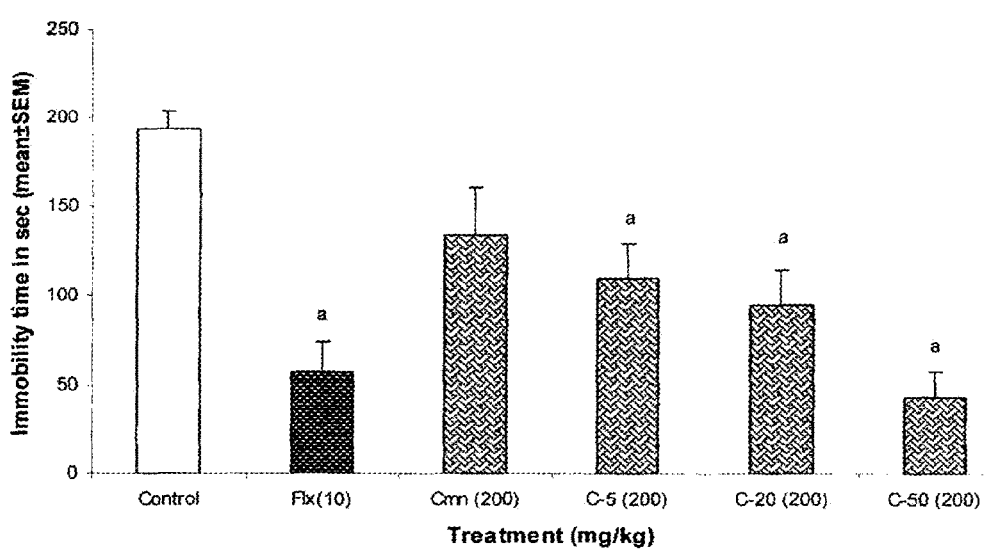
FIG. 3 shows data for immobility period and percentage decrease in the immobility of animals when administered with curcumin (conventional) and the compositions of the present invention, i.e., 2502-DNS-5B (C-5); 2502-DNS-20B (C-20) and 2502-DNS-50B (C-50), at a dose of 200 mg/kg.
Figure 4:
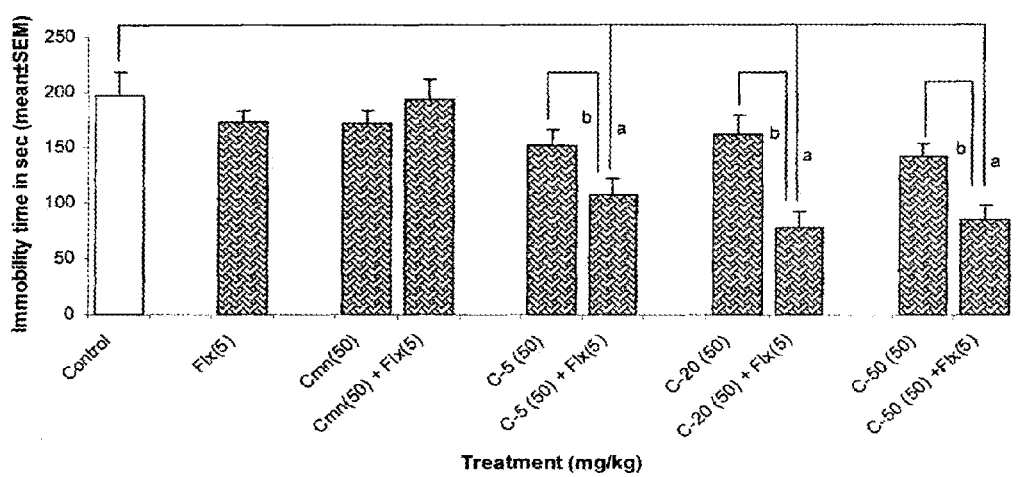
FIG. 4 shows data for immobility period and percentage decrease in the immobility of animals when administered with Fluoxetine (5 mg/kg, ip) with 50 mg/kg of newer formulations, 2502-DNS-5B (C-5); 2502-DNS-20B (C-20) and 2502-DNS-50B (C-50) and conventional curcumin (C-C).
Figure 5:
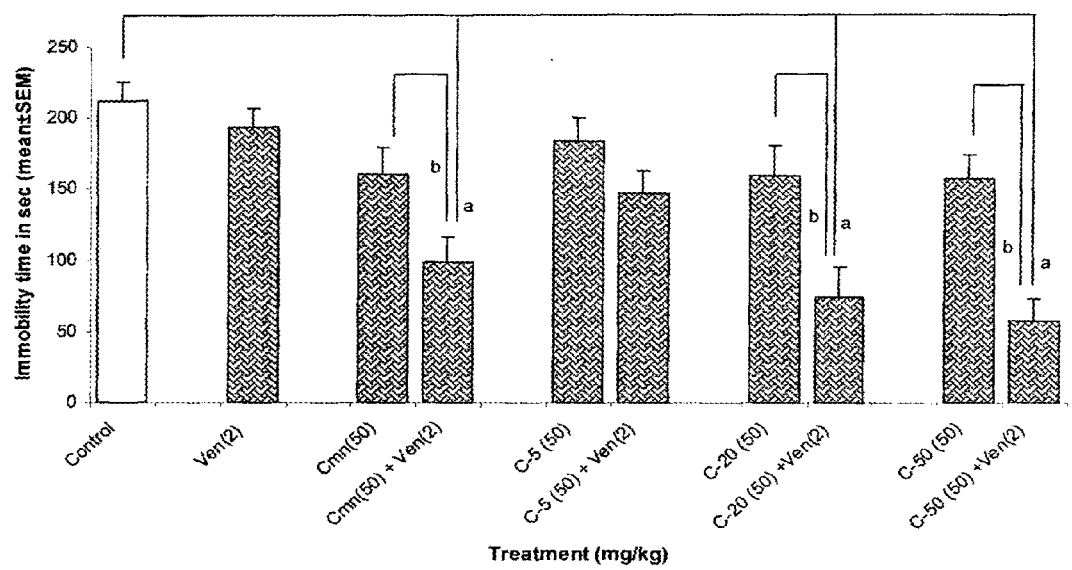
FIG. 5 shows data for immobility period and percentage decrease in the immobility of animals when administered with Venlafaxine (2 mg/kg, ip) with 50 mg/kg of newer formulations C-5 (2502-DNS-5B), C-20 (2502-DNS-20B); and C-50 (2502-DNS-50B) and conventional curcumin.
Figure 6:
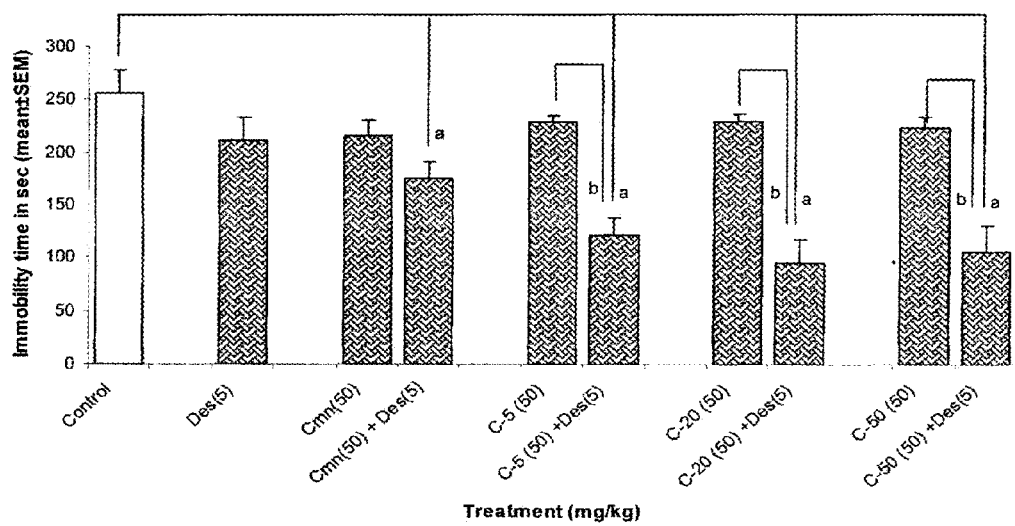
FIG. 6 shows data for immobility period and percentage decrease in the immobility of animals when administered with Desipramine (5 mg/kg, ip) with 50 mg/kg of newer formulations, 2502-DNS-5B (C-5); 2502-DNS-20B (C-20) and 2502-DNS-50B (C-50) and conventional curcumin (C-C).
Figure 7:
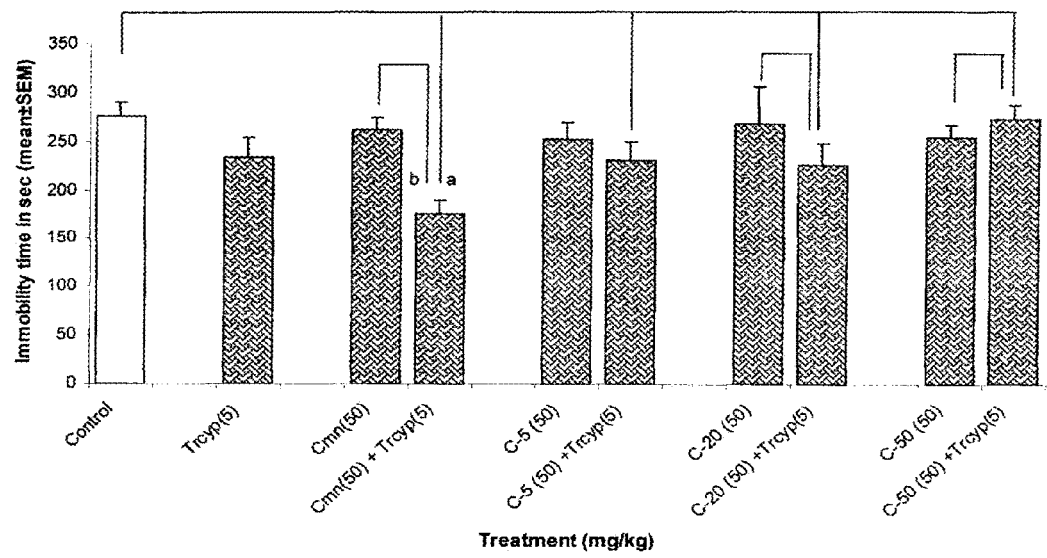
FIG. 7 shows data for immobility period and percentage decrease in the immobility of animals when administered with Tranylcypromine (5 mg/kg, ip) with 50 mg/kg of newer formulations, 2502-DNS-5B (C-5); 2502-DNS-20B (C-20) and 2502-DNS-50B (C-50) and conventional curcumin (C-C).

Tests for antidepressant activity of curcumin were conducted using conventional curcumin (C-C), and the newer compositions of the present invention i.e. 2502-DNS-5B (C-5); 2502-DNS-20B (C-20) and 2502-DNS-50B (C-50) for three doses—50 mg/kg, 100 mg/kg and 200 mg/kg and 10 mg/kg of Flouxetine (Flx). Table 1, Table 2 and Table 3 given below provide data for immobility period and percentage decrease in the immobility of the animals when administered at doses 50 mg/kg, 100 mg/kg and 200 mg/kg respectively. The immobility period data obtained from tables 1, 2 and 3 is plotted against the dose administered in FIG. 1, FIG. 2 and FIG. 3 respectively, as shown in the drawing accompanying this specification.

Test Substances: 50 mg/kg of curcumin (conventional) and the composition of the present invention 2502-DNS-5B (C-5); 2502-DNS-20B (C-20) and 2502-DNS-50B (C-50).
Animals: Male Laca mice.
Test Procedures: Porsolt Forced Swim test. Rectangular glass jar (25×12×25 cm$^3$) containing 15 cm of water maintained at 24±1° C.

TABLE 1

| S. No. | Treatment | Dose (mg/kg) | Immobility period (in seconds) | % Decrease in immobility w.r.t saline treated group |
|---|---|---|---|---|
| 1 | Vehicle Control | 10 ml/kg | 221.83 ± 10.15 | — |
| 2 | Curcumin | 50 (Curcuminoids 47.66 mg) | 171.8 ± 10.87 | 22.55 |
| 3 | 2502-DNS-5B | 50 (Curcuminoids 3.56 mg) | 152 ± 23.26 | 31.47 |
|  | 2502-DNS-20B | 50 (Curcuminoids 11.56 mg) | 161 ± 17.61 | 27.42 |
|  | 2502-DNS-50B | 50 (Curcuminoids 24.05 mg) | 144 ± 12.57 | 35.08 |
| 4 | Fluoxetine | 10 | 57 ± 17.45 | 74.30 |

*p < 0.05 as compared to vehicle treated control

Test Substances: 100 mg/kg of curcumin (conventional) and newer formulations 2502-DNS-5B (C-5); 2502-DNS-20B (C-20) and 2502-DNS-50B (C-50).
Animals: Male Laca mice.
Test Procedures: Porsolt Forced Swim test. Rectangular glass jar (25×12×25 cm3) containing 15 cm of water maintained at 24±1° C.

TABLE 2

| S. No. | Treatment | Dose (mg/kg) | Immobility period (in seconds) | % Decrease in immobility w.r.t saline treated group |
|---|---|---|---|---|
| 1 | Vehicle Control | 10 ml/kg | 193.33 | — |
| 2 | Curcumin | 100 (Curcuminoids 95.25 mg) | 174.2 ± 15.17 | 9.89 |

TABLE 2-continued

| S. No. | Treatment | Dose (mg/kg) | Immobility period (in seconds) | % Decrease in immobility w.r.t saline treated group |
|---|---|---|---|---|
| 3 | 2502-DNS-5B | 100 (Curcuminoids 7.03 mg) | 184.5 ± 23.64 | 4.56 |
|  | 2502-DNS-20B | 100 (Curcuminoids 23.05 mg) | 111 ± 30.01 | 42.58 |
|  | 2502-DNS-50B | 100 (Curcuminoids 48.10 mg) | 49.16 ± 15.63 | 74.57 |
| 4 | Fluoxetine | 10 | 57 ± 17.45 | 70.51 |

*$p < 0.05$ as compared to vehicle treated control

Test Substances: 200 mg/kg of curcumin (conventional) and newer formulations 2502-DNS-5B (C-5); 2502-DNS-20B (C-20) and 2502-DNS-50B (C-50).
Animals: Male Laca mice.
Test Procedures: Porsolt Forced Swim test. Rectangular glass jar (25×12×25 cm3) containing 15 cm of water maintained at 24±1° C.

TABLE 3

| S. No. | Treatment | Dose (mg/kg) | Immobility period (in seconds) | % Decrease in immobility w.r.t saline treated group |
|---|---|---|---|---|
| 1 | Vehicle Control | 10 ml/kg | 193.33 ± 19.82 | — |
| 2 | Curcumin | 200 (Curcuminoids 190.50 mg) | 133.2 ± 26.82 | 31.10 |
| 3 | 2502-DNS-5B | 200 (Curcuminoids 14.06 mg) | 109.33 ± 19.5 | 43.44 |
|  | 2502-DNS-20B | 200 (Curcuminoids 46.10 mg) | 94 ± 19.64 | 51.37 |
|  | 2502-DNS-50B | 200 (Curcuminoids 96.20 mg) | 43.33 ± 13.68 | 77.58 |
| 4 | Fluoxetine | 10 | 57 ± 17.45 | 70.51 |

*$p < 0.05$ as compared to vehicle treated control

The above study shows that, the curcumin compounds, C-5, C-20 and C-50 show maximum response (decrease in immobility time) in forced swimming test (FST) at 45 and 60 min similar to conventional curcumin (C-C). Therefore, 45 min is taken as the time interval in further studies to investigate the interaction of these drugs with several classes of antidepressant drugs acting through varied mechanisms of actions. 50 mg/kg of all these formulations showed uniform immobility period similar to C-C. C-20 and C-50 were more effective at 100 and 200 mg/kg compared to C-5 and C-C. At this dosage, the immobility period was similar to that produced by fluoxetine (10 mg/kg).

Combination with Sub-Effective Doses of Fluoxetine (Table 4)

Test Substances: Fluoxetine (5 mg/kg, ip) with 50 mg/kg of newer formulations, 2502-DNS-5B (C-5); 2502-DNS-20B (C-20) and 2502-DNS-50B (C-50) and conventional curcumin (C-C)
Animals: Male Laca mice.
Test Procedures: Porsolt Forced Swim test. Rectangular glass jar (25×12×25 cm3) containing 15 cm of water maintained at 24±1° C.

comparative data for immobility period and percentage decrease in the immobility of the animals for curcumin (administered at doses 50 mg/kg) when administered with Fluoxetine (5 mg/kg, ip), Venlafaxine (2 mg/kg, ip), Desipramine (5 mg/kg, ip) and Tranylcypromine (5 mg/kg, ip) respectively. The immobility period data obtained from Tables 4, 5, 6 and 7 is plotted against the dose administered in FIG. 4, FIG. 5, FIG. 6 and FIG. 7 respectively, as shown in the drawing accompanying this specification.

TABLE 4

| S. No. | Treatment | Dose (mg/kg) | Immobility period (in seconds) | % Decrease in immobility w.r.t saline group |
|---|---|---|---|---|
| 1 | Vehicle Control | 10 ml/kg | 197 ± 20.94 | — |
| 2. | Fluoxetine | 5 mg/kg | 172.75 ± 10.4 | 12.30 |
| 3 | Curcumin | 50 (Curcuminoids 47.66 mg) | 171.8 ± 10.87 | 12.79 |
|  | Cmn + Flx | 50 + 5 | 192.6 ± 18.34 | 2.23 |
| 4 | 2502-DNS-5B | 50 (Curcuminoids 3.56 mg) | 152 ± 13.26 | 22.84 |
|  | C-5 + Flx | 50 + 5 | 107.25 ± 14.82 | 45.55 |
|  | 2502-DNS-20B | 50 (Curcuminoids 11.56 mg) | 161 ± 17.61 | 18.27 |
|  | C-20 + Flx | 50 + 5 | 77 ± 14.61 | 60.91 |
|  | 2502-DNS-50B | 50 (Curcuminoids 24.05 mg) | 141 ± 12.57 | 28.42 |
|  | C-50 + Flx | 50 + 5 | 84.66 ± 12.96 | 57.02 |

*$p < 0.05$ as compared to vehicle treated control

Combination Studies with Different Antidepressants

Combination studies of curcumin were carried out with different antidepressants available in the market. The comparative data obtained from these studies is tabulated in Tables 4-7. Table 4, Table 5, Table 6 and Table 7 provide Combination Studies with Sub-Effective Doses of Venlafaxine (Table 5)
Test Substances: Venlafaxine (2 mg/kg, ip) with 50 mg/kg of newer formulations C-5 (2502-DNS-5B), C-20 (2502-DNS-20B); and C-50 (2502-DNS-50B) and conventional curcumin Animals: Male Laca mice.
Test Procedures: Porsolt Forced Swim test. Rectangular glass jar (25×12×25 cm3) containing 15 cm of water maintained at 24±1° C.

TABLE 5

| S. No. | Treatment | Dose (mg/kg) | Immobility period (in seconds) | % Decrease in immobility w.r.t vehicle group |
|---|---|---|---|---|
| 1 | Vehicle Control | 10 ml/kg | 212.25 ± 13.51 | — |
| 2. | Venlafaxine | 2 mg/kg | 193.8 ± 13.26 | 8.69 |
| 3 | Curcumin | 50 (Curcuminoids 47.66 mg) | 160.33 ± 19.09 | 24.46 |
|  | Cmn + Ven | 50 + 2 | 98.80 ± 20.19 | 53.45 |
| 4 | 2502-DNS-5B | 50 (Curcuminoids 3.56 mg) | 183.66 ± 16.18 | 13.46 |
|  | C-5 + Ven | 50 + 2 | 147.5 ± 21.29 | 30.50 |
|  | 2502-DNS-20B | 50 (Curcuminoids 11.56 mg) | 159 ± 21.40 | 25.08 |
|  | C-20 + Ven | 50 + 2 | 74.68 ± 20.30 | 64.81 |
|  | 2502-DNS-50B | 50 (Curcuminoids 24.05 mg) | 15;7 ± 16.26 | 26.44 |
|  | C-50 + Ven | 50 + 2 | 57.60 ± 15.01 | 72.86 |

*p < 0.05 as compared to vehicle treated control

Combination Studies with Sub-Effective Doses of Desipramine (Table 6)
Test Substances: Desipramine (5 mg/kg, ip) with 50 mg/kg of newer formulations, 2502-DNS-5B (C-5); 2502-DNS-20B (C-20) and 2502-DNS-50B (C-50) and conventional curcumin (C-C).
Animals: Male Laca mice.
Test Procedures: Porsolt Forced Swim test. Rectangular glass jar (25×12×25 cm3) containing 15 cm of water maintained at 24±1° C.

TABLE 6

| S. No. | Treatment | Dose (mg/kg) | Immobility period (in seconds) | % Decrease in immobility w.r.t vehicle group |
|---|---|---|---|---|
| 1 | Vehicle Control | 10 ml/kg | 256.25 ± 21.40 | — |
| 2. | Desipramine | 5 mg/kg | 211.5 ± 21.97 | 17.46 |
| 3 | Curcumin | 50 (Curcuminoids 47.66 mg) | 215.50 ± 13.97 | 15.90 |
|  | Cmn + Des | 50 + 5 | 175.16 ± 15.30 | 31.64 |
| 4 | 2502-DNS-5B | 50 (Curcuminoids 3.56 mg) | 228.66 ± 6.22 | 10.76 |
|  | C-5 + Des | 50 + 5 | 120.80 ± 15.89 | 52.85 |
|  | 2502-DNS-20B | 50 (Curcuminoids 11.56 mg) | 229.25 ± 7.21 | 10.53 |
|  | C-20 + Des | 50 + 5 | 95.33 ± 20.45 | 62.79 |
|  | 2502-DNS-50B | 50 (Curcuminoids 24.05 mg) | 223.50 ± 8.99 | 12.78 |
|  | C-50 + Des | 50 + 5 | 105.50 ± 23.94 | 58.82 |

*p < 0.05 as compared to vehicle treated control

Combination Studies with Sub-Effective Doses of Tranylcypromine (Table 7)
Test Substances: Tranylcypromine (5 mg/kg, ip) with 50 mg/kg of newer formulations, 2502-DNS-5B (C-5); 2502-DNS-20B (C-20) and 2502-DNS-50B (C-50) and conventional curcumin (C-C).

Animals: Male Laca mice.

Test Procedures: Porsolt Forced Swim test. Rectangular glass jar (25×12×25 cm3) containing 15 cm of water maintained at 24±1° C.

TABLE 7

| S. No. | Treatment | Dose (mg/kg) | Immobility period (in seconds) | % Decrease in immobility w.r.t vehicle group |
|---|---|---|---|---|
| 1 | Vehicle Control | 10 ml/kg | 275.80 ± 15.19 | — |
| 2. | Tranylcypromine | 5 mg/kg | 234 ± 20.41 | 15.15 |
| 3 | Curcumin | 50 (Curcuminoids 47.66 mg) | 262.25 ± 11.89 | 4.91 |
|  | Cmn + Trycp | 50 + 5 | 231.5 ± 18.47 | 15.90 |
| 4 | 2502-DNS-5B | 50 (Curcuminoids 3.56 mg) | 252.75 ± 16.86 | 8.35 |
|  | C-5 + Trycp | 50 + 5 | 219.5 ± 13.11 | 20.41 |
|  | 2502-DNS-20B | 50 (Curcuminoids 11.56 mg) | 268 ± 37.54 | 2.82 |
|  | C-20 + Trycp | 50 + 5 | 225.83 ± 22.59 | 18.11 |
|  | 2502-DNS-50B | 50 (Curcuminoids 24.05 mg) | 253.8 ± 12.57 | 7.97 |
|  | C-50 + Trycp | 50 + 5 | 272.60 ± 14.10 | 1.16 |

*p < 0.05 as compared to vehicle treated control

Conclusion 50 mg/kg was taken as the sub-effective dose for combination studies with different antidepressants. With sub-effective dose of fluoxetine (5 mg/kg, selective serotonin reuptake inhibitor), 50 mg/kg of all the curcumin formulations of the present invention potentiated the decrease in immobility time in FST. With sub-effective dose of venlafaxine (2 mg/kg, a dual reuptake inhibitor of serotonin and norepinephrine), C-20 and C-50 were more effective and showed potentiated antidepressant effect similar to that observed with C-C the percentage inhibition in the immobility time was 10% more in case of C-20 and 20% in case of C-50 compared to C-C. In this test, C-5 did not show any potentiation with venlafaxine. With sub-effective dose of desipramine (5 mg/kg, a tricyclic antidepressant), all the three newer formulations curcumin i.e. C-5, C-20 and C-50 showed a potentiated antidepressant activity. The sub-effective dose of C-C failed to show any potentiation with desipramine. None of the newer curcumin formulations (C-5, C-20, C-50) or C-C showed potentiated effect with sub-effective dose of tranylcypromine (5 mg/kg, a nonspecific MAO inhibitor).

B. HPLC Data of Compounds 100 mg/kg dose of all newer curcumin formulations i.e. C-5, C-20, C-50 and Conventional curcumin C-C were injected to the animals and were sacrificed later after 45 min for studying the changes in biological amine levels using HPLC.

Test Substances: Fluoxetine, standard conventional curcumin (100 mg/kg), newer curcumin formulations (100 mg/kg each)
Animals: Male Laca mice.
Test Procedures: Animals were sacrificed after 45 min of drug administration similar to the time period of behavioral observations.
HPLC-ECD detector: Mobile phase—Phosphate buffer: Acetonitrile (87:13), pH 4.5
  Column—ODS-3 C-18 column (250×4.6 mm I.D.; 5 μm particle size)

TABLE 8

| Treatment (n = 5) | Dose (mg/kg) | Norepinephrine (ng/mg tissue) | Dopamine (ng/mg tissue) | 5-hydroxytryptamine (ng/mg tissue) |
|---|---|---|---|---|
| Control | — | 2.96 ± 0.37 | 5.43 ± 0.43 | 3.97 ± 0.86 |
| Fluoxetine | 10 | 4.17 ± 0.23a | 6.09 ± 0.54 | 5.42 ± 0.13 |
| Curcumin | 100 (Curcuminoids 95.25 mg) | 4.97 ± 0.33a | 4.33 ± 0.58 | 4.24 ± 0.56 |
| C-5 | 100 (Curcuminoids 7.03 mg) | 4.83 ± 0.13a | 7.41 ± 0.26a | 6.02 ± 0.53a |
| C-20 | 100 (Curcuminoids 23.05 mg) | 4.20 ± 0.14a | 6.57 ± 0.20 | 6.32 ± 0.24a |
| C-50 | 100 (Curcuminoids 48.10 mg) | 3.04 ± 0.56 | 5.76 ± 0.60 | 5.56 ± 0.67 |

TABLE 9

| Treatment (n = 5) | Dose (mg/kg) | Dopamine (ng/mg tissue) | % increase w.r.t Control | % increase w.r.t Fluoxetine | % increase w.r.t Curcumin |
|---|---|---|---|---|---|
| Control | — | 5.43 ± 0.43 | 0 | — | — |
| Fluoxetine | 10 | 6.09 ± 0.54 | 12.15 | — | — |
| Curcumin | 100 (Curcuminoids 95.25 mg) | 4.33 ± 0.58 | −20.25 | −21.77 | — |
| C-5 | 100 (Curcuminoids 7.03 mg) | 7.41 ± 0.26a | 36.46 | 21.67 | 71.13 |
| C-20 | 100 (Curcuminoids 23.05 mg) | 6.57 ± 0.20 | 20.99 | 7.88 | 51.73 |
| C-50 | 100 (Curcuminoids 48.10 mg) | 5.76 ± 0.60 | 6.07 | −5.41 | 33.02 |

TABLE 10

| Treatment (n = 5) | Dose (mg/kg) | 5-hydroxytryptamine (ng/mg tissue) | % increase w.r.t Control | % increase w.r.t Fluoxetine | % increase w.r.t Curcumin |
|---|---|---|---|---|---|
| Control | — | 3.97 ± 0.86 | 0 | — | — |
| Fluoxetine | 10 | 5.42 ± 0.13 | 36.52 | — | — |
| Curcumin | 100 (Curcuminoids 95.25 mg) | 4.24 ± 0.56 | 6.80 | −21.77 | — |
| C-5 | 100 (Curcuminoids 7.03 mg) | 6.02 ± 0.53a | 51.63 | 11.07 | 41.98 |
| C-20 | 100 (Curcuminoids 23.05 mg) | 6.32 ± 0.24a | 59.19 | 16.60 | 49.05 |
| C-50 | 100 (Curcuminoids 48.10 mg) | 5.56 ± 0.67 | 40.05 | 2.58 | 31.13 |

TABLE 11

| Treatment (n = 5) | Dose (mg/kg) | Norepinephrine (ng/mg tissue) | % increase w.r.t Control | % increase w.r.t Fluoxetine | % increase w.r.t Curcumin |
|---|---|---|---|---|---|
| Control | — | 2.96 ± 0.33 | 0 | — | — |
| Fluoxetine | 10 | 4.17 ± 0.23a | 40.87 | — | — |
| Curcumin | 100 (Curcuminoids 95.25 mg) | 4.97 ± 0.33a | 67.90 | 19.18 | — |
| C-5 | 100 (Curcuminoids 7.03 mg) | 4.83 ± 0.13a | 63.17 | 15.82 | −2.81 |
| C-20 | 100 (Curcuminoids 23.05 mg) | 4.20 ± 0.14a | 41.89 | 0.71 | −15.49 |
| C-50 | 100 (Curcuminoids 48.10 mg) | 3.04 ± 0.56 | 2.70 | −27.09 | −38.83 |

Conclusion

C-5 showed a significant increase (20.99%) in the dopamine levels compared to control. The increase in dopamine levels compared to C-C is 71.13, 51.73, and 33.02 in case of C-5, C-20 and C-50 respectively. C-5 and C-20 showed a significant increase (51.63 and 59.19) in 5-HT levels compared to control. The increase in 5-HT levels compared to C-C is 41.98, 49.05, and 31.13 in case of C-5, C-20 and C-50 respectively. C-5 and C-20 showed a significant increase (63.17 and 41.84) in norepinephrine levels compared to control. The increase in norepinephrine levels was similar to that observed in the C-C treatment group.

Example 6

Comparative Bioavailability Study

The bioavailability study was conducted at Amala Cancer Institute, Thrissur, Kerala on a request from the applicant. Twelve healthy subjects were recruited for the purpose of the study. All the volunteers were asked to abstain from Curcumin rich foods during the course of the study. The study design chosen was a balanced, open label, two-treatment, two-period, single dose, bioavailability study.

12 Subject were recruited for the study and were asked to avoid consumption of food containing rich turmeric powder or extract for 24 hours preceding each period. A single dose of Curcumin capsules (equivalent to 1 gm of curcuminoids) were used for the study. The following supplements were used for the purpose of the study:

Supplement 1—comprising Curcumin extract powder 95% i.e. C-C (500 mg Capsule equivalent to 1 gm of curcuminoids) of OmniActive Health Technologies Ltd., India was administered as a single dose of two capsules of Curcumin extract powder 95% 500 mg.

Supplement 2—comprising Curcumin Ultrasol Dry Nutrient System 50% i.e C-50 (250 mg Capsule equivalent to 1 gm of curcuminoids) of OmniActive Health Technologies Ltd., India was administered as a single dose of four capsules of Curcumin Ultrasol Dry Nutrient System 50% 250 mg.

Each of the supplements were administered with 240 ml water in each period.

Methodology:

The primary aim of this study was to compare the bioavailability of Curcumin after administration of a single dose of two Curcumin extract powder 95% (500 mg Capsule equivalent to 1 gm of curcuminoids) with four Curcumin Ultrasol Dry Nutrient System 50% i.e C-50 (250 mg Capsule equivalent to 1 gm of curcuminoids) in healthy human subjects.

The secondary aim of study was to monitor the safety and tolerability of a single dose of 1 g curcuminoids when administered in 12 healthy human subjects.

The study design is open label, two-treatment, two-period, single dose, bioavailability study. In this study 12 subjects were recruited and all of them completed the study. Subjects were asked to avoid consumption of food containing rich turmeric powder or extract for 24 hours preceding each period. A single dose of Curcumin capsules equivalent to 1 gm of curcuminoids: Supplement 1 or Supplement 2 was administered with 240 ml water in each period. There was a washout period of at least 2 weeks between the doses.

Blood was drawn from each subject just prior to dosing and at 1, 2, 4, 6, 8, and 24 hours post-dose. The total blood loss for each subject was approximately 70 ml and there were totally 14 blood samples of 5 ml each time point throughout the study. The blood samples drawn at different time intervals are centrifuged and the curcumin in plasma is measured through HPLC technique.

The primary efficacy variables were measured in this study were $C_{max}$, AUCO-t and AUCO-$\infty$ and the secondary efficacy variable were as follows $T_{max}$, $T\frac{1}{2}$ and Kel. The statistical evaluation was done by Winnonlin Software 5.0.1 version. Outcome variables: From the plasma sample analysis time versus concentration were plotted from which $C_{max}$ (maximum concentration of curcumin in blood) were calculated. From the peak obtained, AUC for 24 hrs were calculated. $T_{max}$ and $T\frac{1}{2}$ were also be recorded and compared for the two products.

Method of Analysis:

Preparation of Standard Stock Solution (157489.2 ng/ml)

Standard Name: Turmeric Standardized Extract and the standard purity is 96.03% (From Kancor, Angamaly, Kerala).

16.4 mg of Turmeric standardized extract was weighed in 100 ml volumetric flask. Dissolved and make up the volume with methanol.

Preparation of Standard Solution A (15748.92 ng/ml): 10.0 mL of standard stock solution was taken and diluted to 100 mL with methanol.

Preparation of Standard Solution B (787.446 ng/ml): 1.0 mL of standard solution A was taken and diluted to 20 mL with methanol.

Preparation of Final Standard Solution C (393.723 ng/ml): 5.0 mL of standard solution B was taken and diluted to 10 mL with methanol.

Preparation of Standard Solution D (3149.784 ng/ml): 5.0 mL of solution A was taken and diluted to 25 mL with methanol Preparation of Spiking Standard Solution E (1574.892 ng/ml): 5.0 mL of solution D was taken and diluted to 10 mL with methanol.

Preparation of Blank (Spiked with Standard Solution E): Each blank plasma samples was allowed to attain the room temperature. 1.0 ml of blank plasma sample and 100 µl of spiking standard solution E was mixed in a cleaned glass test tube. This spiked blank solution was then extracted using the same procedure as that of sample.

Preparation of Standard (Spiked with Standard Solution E): Pipette out 900 μl of blank plasma and 100 μl of standard solution D in a cleaned glass test tube. To this 100 μl of spiking standard solution E was added and mixed. This spiked standard was then extracted using the same procedure as that of sample.

Preparation of Sample (Spiked with Standard Solution E): The frozen plasma samples were allowed to attain the room temperature. 1000 μl of the plasma sample was pipetted out and spiked with 100 μl of spiking standard solution E. This solution was vortex for 1 minute and 3.0 ml ethyl acetate (HPLC Grade) was added to the above solutions. The solution was vortex again for 1 minute with the aid of cyclomixer and allowed to settle down at room temperature.

1.5 ml of the upper ethyl acetate layer was pipetted out and evaporated to dryness using vacuum. The dried sample was dissolved in 600 μl of methanol (HPLC Grade) using vortex mixer. This solution was filtered by 0.2 micron membrane filter paper. 100 μl of these filtered solution was injected in HPLC (Waters Alliance System with 2996 PDA detector in isocratic mode). The column used was LiChrospher 100 RP-18 (250×4.6 mm 5 μM particle size) with methanol as the mobile phase and the detection wavelength was 420 nm. To identify and quantized curcuminoids in plasma the chromatographic peaks were compared with standard solution.

Results:

The results obtained from the study conducted as described hereinabove, were tabulated. Tables 12 to 17 below show the data as obtained.

TABLE 12

Individual Concentration Table for Curcumin Extract Powder 95% (ng/mL)

| Subject | Time (hr) | | | | | | |
|---|---|---|---|---|---|---|---|
| | 0.00 | 1.00 | 2.00 | 4.00 | 6.00 | 8.00 | 24.00 |
| 1 | 0.00 | 20.58 | 19.82 | ND | ND | 36.11 | ND |
| 2 | 0.00 | 0.85 | 14.94 | ND | 2.77 | ND | 0.53 |
| 3 | ND | ND | ND | ND | ND | ND | ND |
| 4 | 0.00 | ND | ND | ND | ND | ND | ND |
| 5 | ND | ND | ND | ND | ND | ND | ND |
| 6 | 0.00 | 2.48 | ND | 0.75 | ND | ND | 2.47 |
| 7 | 0.00 | 7.99 | ND | 4.53 | 2.05 | 1.19 | 1.39 |
| 8 | 0.00 | ND | ND | 15.62 | ND | ND | ND |
| 9 | 0.00 | 0.84 | 8.39 | 7.09 | 4.87 | ND | 0.65 |
| 10 | ND | ND | ND | ND | ND | ND | ND |
| 11 | 0.00 | 0.05 | ND | 7.36 | ND | ND | 9.09 |
| 12 | 0.00 | ND | ND | ND | ND | ND | 11.49 |
| N | 9 | 6 | 3 | 5 | 3 | 2 | 6 |
| Mean | 0.000 | 5.464 | 14.384 | 7.071 | 3.232 | 18.650 | 4.270 |
| SD | 0.000 | 7.946 | 5.737 | 5.467 | 1.465 | 24.690 | 4.774 |
| Min | 0.00 | 0.05 | 8.39 | 0.75 | 2.05 | 1.19 | 0.53 |
| Median | 0.00 | 1.66 | 14.94 | 7.09 | 2.77 | 18.65 | 1.93 |
| Max | 0.00 | 20.58 | 19.82 | 15.62 | 4.87 | 36.11 | 11.49 |
| CV % | 0.00 | 145.4 | 39.9 | 77.3 | 45.3 | 132.4 | 111.8 |
| Geometric Mean | 0.00 | 1.582 | 13.544 | 4.886 | 3.026 | 6.557 | 2.233 |

ND—Not Detectable in Plasma

TABLE 13

Mean Concentration Table for Curcumin Extract Powder (min 95% Curcuminoids)

| Time (hr) | Sample | N | Nmiss | Nobs | Mean (ng/mL) |
|---|---|---|---|---|---|
| 0 | Curcumin Powder 95% | 9 | 3 | 12 | 0.0000 |
| 1 | Curcumin Powder 95% | 6 | 6 | 12 | 5.4638 |
| 2 | Curcumin Powder 95% | 3 | 9 | 12 | 14.3842 |
| 4 | Curcumin Powder 95% | 5 | 7 | 12 | 7.0711 |
| 6 | Curcumin Powder 95% | 3 | 9 | 12 | 3.2316 |
| 8 | Curcumin Powder 95% | 2 | 10 | 12 | 18.6496 |
| 24 | Curcumin Powder 95% | 6 | 6 | 12 | 4.2698 |

TABLE 14

PK Parameter for Curcumin Extract Powder (min 95% Curcuminoids)

| Subject | Cmax ng/ml | Tmax Hr | AUCT ng/ml * h | AUCINF ng/ml * h | Kel hr | Thalf hr |
|---|---|---|---|---|---|---|
| 1 | 36.11 | 8.00 | 198.27 | ND | ND | ND |
| 2 | 14.94 | 2.00 | 73.46 | 77.46 | 0.13 | 5.21 |
| 3 | ND | ND | ND | ND | ND | ND |
| 4 | ND | ND | ND | ND | ND | ND |
| 5 | ND | ND | ND | ND | ND | ND |
| 6 | 2.48 | 1.00 | 38.31 | ND | ND | ND |
| 7 | 7.99 | 1.00 | 53.25 | 76.09 | 0.06 | 11.39 |
| 8 | 15.62 | 4.00 | 31.24 | ND | ND | ND |
| 9 | 8.39 | 2.00 | 82.17 | 87.74 | 0.12 | 5.95 |
| 10 | ND | ND | ND | ND | ND | ND |
| 11 | 9.09 | 24.00 | 175.60 | ND | ND | ND |
| 12 | 11.49 | 24.00 | 137.89 | ND | ND | ND |
| N | 8 | 8 | 8 | 3 | 3 | 3 |
| Mean | 13.263 | 8.250 | 98.774 | 80.433 | 0.104 | 7.516 |
| SD | 10.133 | 9.982 | 63.848 | 6.368 | 0.038 | 3.380 |
| Min | 2.48 | 1.00 | 31.24 | 76.09 | 0.06 | 5.21 |
| Median | 10.29 | 3.00 | 77.81 | 77.46 | 0.12 | 5.95 |
| Max | 36.11 | 24.00 | 198.27 | 87.74 | 0.13 | 11.39 |
| CV % | 76.4 | 121.0 | 64.6 | 7.9 | 36.6 | 45.0 |
| Geometric Mean | 10.486 | 4.059 | 80.968 | 80.269 | 0.098 | 7.066 |

ND—Not Detectable

TABLE 15

Individual Concentration Table for UltraSol Nutrient System (50% Curcuminoids) (ng/mL)

| Subject | Time (hr) | | | | | | |
|---|---|---|---|---|---|---|---|
| | 0.00 | 1.00 | 2.00 | 4.00 | 6.00 | 8.00 | 24.00 |
| 1 | 0.00 | 46.04 | 26.57 | 12.65 | 0.00 | 3.78 | 4.52 |
| 2 | 0.00 | 10.03 | 19.41 | 5.41 | 5.65 | 0.00 | 0.75 |
| 3 | ND | ND | ND | ND | ND | ND | ND |
| 4 | 0.00 | 15.58 | 0.00 | 16.11 | 4.94 | 1.50 | 0.76 |
| 5 | ND | ND | ND | ND | ND | ND | ND |
| 6 | 0.00 | 2.56 | 12.73 | 39.58 | 1.38 | 7.55 | 7.85 |
| 7 | 0.00 | 10.24 | 19.18 | 8.87 | 9.78 | 4.20 | 2.74 |
| 8 | 0.00 | 32.10 | 2.99 | 10.20 | 11.55 | 8.07 | 2.76 |
| 9 | 0.00 | 16.08 | 20.32 | 35.51 | 1.69 | 9.55 | 2.88 |
| 10 | ND | ND | ND | ND | ND | ND | ND |
| 11 | 0.00 | 24.47 | 41.21 | 33.47 | 10.39 | 35.27 | 23.12 |
| 12 | 0.00 | 32.98 | 22.70 | 7.03 | 1.66 | 5.88 | 5.31 |
| N | 9 | 9 | 9 | 9 | 9 | 9 | 9 |
| Mean | 0.000 | 21.120 | 18.346 | 18.759 | 5.227 | 8.422 | 5.632 |
| SD | 0.000 | 13.854 | 12.344 | 13.517 | 4.401 | 10.534 | 6.927 |
| Min | 0.00 | 2.56 | 0.00 | 5.41 | 0.00 | 0.00 | 0.75 |
| Median | 0.00 | 16.08 | 19.41 | 12.65 | 4.94 | 5.88 | 2.88 |
| Max | 0.00 | 46.04 | 41.21 | 39.58 | 11.55 | 35.27 | 23.12 |
| CV % | 0.00 | 65.6 | 67.3 | 72.1 | 84.2 | 125.1 | 123.0 |
| Geometric Mean | 0.00 | 16.240 | Missing | 14.747 | Missing | Missing | 3.357 |

ND—Not Detectable

TABLE 16

Mean Concentration Table for UltraSol Nutrient System (50% Curcuminoids)

| Time (hr) | Sample | N | Nmiss | Nobs | Mean (ng/mL) |
|---|---|---|---|---|---|
| 0 | Curcumin DNS 50% | 9 | 3 | 12 | 0.0000 |
| 1 | Curcumin DNS 50% | 9 | 3 | 12 | 21.1200 |
| 2 | Curcumin DNS 50% | 9 | 3 | 12 | 18.3456 |
| 4 | Curcumin DNS 50% | 9 | 3 | 12 | 18.7589 |
| 6 | Curcumin DNS 50% | 9 | 3 | 12 | 5.2267 |
| 8 | Curcumin DNS 50% | 9 | 3 | 12 | 8.4222 |
| 24 | Curcumin DNS 50% | 9 | 3 | 12 | 5.6322 |

TABLE 17

PK Parameter for UltraSol Nutrient System (50% Curcuminoids)

| Subject | Cmax ng/ml | Tmax Hr | AUCT ng/ml * h | AUCINF ng/ml * h | Kel hr | Thalf hr |
|---|---|---|---|---|---|---|
| 1 | 46.04 | 1.00 | 181.38 | 235.13 | 0.08 | 8.24 |
| 2 | 19.41 | 2.00 | 67.27 | 74.47 | 0.10 | 6.66 |
| 3 | ND | ND | ND | ND | ND | ND |
| 4 | 16.11 | 4.00 | 77.26 | 83.62 | 0.12 | 5.80 |
| 5 | ND | ND | ND | ND | ND | ND |
| 6 | 39.58 | 4.00 | 234.33 | 993.49 | 0.01 | 67.03 |
| 7 | 19.18 | 2.00 | 136.03 | 173.18 | 0.07 | 9.40 |
| 8 | 32.10 | 1.00 | 174.80 | 211.72 | 0.07 | 9.27 |
| 9 | 35.51 | 4.00 | 229.95 | 272.66 | 0.07 | 10.28 |
| 10 | ND | ND | ND | ND | ND | ND |
| 11 | 41.21 | 2.00 | 676.40 | 2553.06 | 0.01 | 56.26 |
| 12 | 32.98 | 1.00 | 179.81 | 280.03 | 0.05 | 13.08 |
| N | 9 | 9 | 9 | 9 | 9 | 9 |
| Mean | 31.347 | 2.333 | 217.467 | 541.929 | 0.067 | 20.671 |
| SD | 10.748 | 1.323 | 181.813 | 802.914 | 0.037 | 23.480 |
| Min | 16.11 | 1.00 | 67.27 | 74.47 | 0.01 | 5.80 |
| Median | 32.98 | 2.00 | 179.81 | 235.13 | 0.07 | 9.40 |
| Max | 46.04 | 4.00 | 676.40 | 2553.06 | 0.12 | 67.03 |
| CV % | 34.3 | 56.7 | 83.6 | 148.2 | 55.5 | 113.6 |
| Geometric Mean | 29.502 | 2.000 | 174.089 | 279.463 | 0.052 | 13.416 |

ND—Not Detectable

Conclusion

Prior art indicates that curcumin is poorly absorbed upon oral administration. With the oral administration of 3.6 g of curcumin, about 11 ng/ml was measurable in plasma. Special efforts/techniques are required to detect curcumin in plasma at lower doses. However, in the current study, 1 g of curcumin was administered orally to all subjects in two periods for both supplementations. As mentioned above this 1 gm dose was very low to detect Curcumin in plasma samples, the plasma samples were externally spiked with 25 ng of curcumin to facilitate its measurement in HPLC. After quantification of Curcumin in plasma the total area of chromatogram is subtracted with area of 25 ng of externally spiked Curcumin to arrive at the curcumin concentration.

The bioanalysis results showed that curcumin was not present in majority of blood sampling time points in Curcumin supplementation group. In case of UltraSol DNS Curcumin supplementation almost all sampling time points curcumin were measurable, the average serum concentration up to 21 ng/ml was measured. Curcumin extract powder 95% (Actual Curcuminoids content 95.2%) has 1.98 times higher curcuminoids content compared to UltraSol DNS Curcumin 50% Powder (Actual Curcuminoids content 48.17%). In both the curcumin supplements, curcuminoids contents were equal i.e 1 gm.

The mean AUC for Curcumin Ultrasol Nutrient System 50% is 541.93 ng/ml*h and for Curcumin extract powder 95% is 80.43 ng/ml*h as shown in FIG. 8. Curcumin Ultrasol Nutrient System 50% AUC shows 6.74 folds increase than Curcumin extract powder 95%, which indicates that Ultrasol Nutrient System has higher bioavailability (6.74 times) compared to Curcumin extract powder 95%.

In comparison to Biocurcumax, showed 6.93 higher bioavailability compared to Curcumin powder this increase is with a dose of 2 gm/d.2 But in current study UltraSol DNS Curcumin showed 6.74 times higher bioavailability compared to plain curcumin powder even with the dose of 1 gm/d which is half of the Biocurcumax dose. Thus, the Ultrasol Nutrient System, Curcumin Dry Powder 50% formulation demonstrates higher absorption compared to Curcumin powder 95% at the same dose level.

The peak median concentration i.e Tmax achieved by Ultrasol DNS 50% is 2 hour and for Curcumin extract powder 95% is 3 hour, it may indicate that Ultrasol DNS Curcumin have faster onset of action than Curcumin powder extract.

Safety: The given dose of curcumin 1 gm in both 95% powder and Ultrasol DNS 50% forms, were well tolerated in all subjects and there were no adverse events reported during the entire course of study.

From the details given above it can be observed that the composition of the present invention is not a mere admixture resulting in a composition which having the aggregation of the properties of the components used but a composition formed by the synergistic activities of the components used Advantages of the Invention The novel water soluble composition of the present invention
1. Exhibits enhanced bioavailability typically useful for alleviating depression.
2. Has no toxicity
3. Can be easily formulated in orally administrable forms such as tablets, capsules, blended powders, etc.
4. Useful in oral delivery of curcumin in high doses for the applications such as antidepressant.

We claim:
1. A water-soluble composition comprising
   curcumin,
   an antioxidant comprising natural tocopherols and ascorbyl palmitate,
   a hydrophilic carrier comprising hydroxy propyl methyl cellulose, and
   a fat,
   wherein the amount of the antioxidant ranges from 1% to 10% by weight of the total composition, the amount of the hydrophilic carrier ranges from 10% to 90% by weight of the total composition, and the amount of the fat ranges from 1% to 25% by weight of the total composition.
2. The composition of claim 1, wherein the curcumin ranges from 1% to about 90% by weight of the total composition.
3. The composition of claim 1, wherein the antioxidant is further selected from the group consisting of rosemary extract, epigallocatechin gallate, catechins, ascorbic acid and mixtures thereof.
4. The composition of claim 1, wherein the hydrophilic carrier is further selected from the group consisting of soluble starch, sodium carboxy methyl cellulose, polyvinyl pyrrolidone, polyethylene glycols, glycerol, sorbitol, mannitol, glucose, sugar and mixtures thereof.

5. The composition of claim 1, wherein the fat is selected from the group consisting of milk fat, medium chain triglycerides, long chain triglycerides, hydrogenated vegetable oils, and mixtures thereof.

6. A method for preparing the composition of claim 1, comprising:
 (i) dissolving the curcumin, the antioxidant, the hydrophilic carrier, and the fat in a solvent to form a homogenous mass;
 (ii) warming the mass to a temperature ranging from about 25° C. to about 60° C. for a period of 4 to 8 hours to obtain a dry wet mass;
 (iii) removing the solvent by evaporation to form a dry mass; and
 (iv) pulverizing the dry mass to form a water-soluble powder.

7. The method of claim 6, wherein the curcumin has a purity content ranging from 50% to 99% by weight.

8. The method of claim 6, wherein the antioxidant is further selected from the group consisting of rosemary extract, epigallocatechin gallate, catechins, ascorbic acid and mixtures thereof.

9. The method of claim 6, wherein the hydrophilic carrier is further selected from the group consisting of soluble starch, sodium carboxy methyl cellulose, polyvinyl pyrrolidone, polyethylene glycols, glycerol, sorbitol, mannitol, glucose, sugar and mixtures thereof.

10. The method of claim 6, wherein the fat is selected from milk fat, medium chain triglycerides, long chain triglycerides, hydrogenated vegetable oils, or mixtures thereof.

11. The method of claim 6, wherein the solvent is selected from the group consisting of isopropyl alcohol, acetone, methanol, alcohol, and mixtures thereof.

12. The composition of claim 1, wherein the curcumin has a purity content ranging from 50% to 99% by weight.

13. The composition of claim 1, wherein the bioavailability of curcumin in the composition is greater than in a control composition comprising curcumin.

14. The method of claim 6, wherein the bioavailability of curcumin is greater than in a control composition comprising curcumin.

15. A method of treating depression comprising administering to a subject in need thereof a therapeutically effective amount of the composition of claim 1.

16. An oral pharmaceutical formulation comprising the composition of claim 1.

17. The composition of claim 1, wherein the hydrophilic carrier further comprises polyvinyl pyrrolidone.

18. A water-soluble composition comprising
 curcumin,
 an antioxidant comprising epigallocatechin gallate and ascorbyl palmitate,
 a hydrophilic carrier comprising polyvinyl pyrrolidone, and
 a fat,
 wherein the amount of the antioxidant ranges from 1% to 10% by weight of the total composition, the amount of the hydrophilic carrier ranges from 10% to 90% by weight of the total composition, and the amount of the fat ranges from 1% to 25% by weight of the total composition.

19. The composition of claim 18, which when administered to a subject in a single dose of 1 g, provides at least one property selected from the group consisting of an area under the curve of 74.47 ng/mL*h and a Cmax of 16.11 ng/mL.

* * * * *